(12) United States Patent
Some (10) Patent No.: US 6,686,602 B2
(45) Date of Patent: Feb. 3, 2004

(54) PATTERNED WAFER INSPECTION USING SPATIAL FILTERING

(75) Inventor: Daniel I. Some, Ashdod (IL)

(73) Assignee: Applied Materials, Inc., Santa Clara, CA (US)

( * ) Notice: Subject to any disclaimer, the term of this patent is extended or adjusted under 35 U.S.C. 154(b) by 7 days.

(21) Appl. No.: 10/050,890

(22) Filed: Jan. 15, 2002

(65) Prior Publication Data

US 2003/0132405 A1 Jul. 17, 2003

(51) Int. Cl.$^7$ ............................................. G01N 21/88
(52) U.S. Cl. ........................... 250/559.45; 250/559.4; 250/559.46; 356/237.1; 356/239.3; 356/239.7; 359/214
(58) Field of Search ................. 250/559.45, 559.41, 250/559.46, 559.4, 226, 216; 356/239.3, 338, 429, 430, 237.1, 238.1, 238.2, 238.3, 239.7; 359/212, 213, 214

(56) References Cited

U.S. PATENT DOCUMENTS

| | | | |
|---|---|---|---|
| 3,614,232 A | 10/1971 | Mathisen | |
| 4,220,976 A * | 9/1980 | Koch | 348/306 |
| 4,370,024 A | 1/1983 | Task et al. | |
| 5,177,559 A | 1/1993 | Batchelder et al. | |
| 5,276,498 A | 1/1994 | Galbraith et al. | |
| 5,309,239 A * | 5/1994 | Bouwhuis | 348/265 |
| 5,359,407 A * | 10/1994 | Suzuki et al. | 356/237.2 |
| 5,506,676 A * | 4/1996 | Hendler et al. | 356/237.1 |
| 5,546,181 A * | 8/1996 | Kobayashi et al. | 356/237.5 |
| 5,617,203 A * | 4/1997 | Kobayashi et al. | 356/237.5 |
| 5,659,390 A | 8/1997 | Danko | |
| 5,784,189 A | 7/1998 | Bozler et al. | |
| 5,808,384 A | 9/1998 | Tabat et al. | |
| 6,248,509 B1 | 6/2001 | Sanford | |
| 6,248,988 B1 * | 6/2001 | Krantz | 250/201.3 |
| 6,288,824 B1 | 9/2001 | Kastalsky | |
| 6,313,937 B1 | 11/2001 | Dowe et al. | |
| 6,329,967 B1 | 12/2001 | Little et al. | |
| 6,392,748 B1 * | 5/2002 | Fateley | 356/330 |

OTHER PUBLICATIONS

U.S. patent application No.: 09/595,902, entitled: "Optical Inspection Method and Apparatus Utilizing a Collection Angle Design".

* cited by examiner

Primary Examiner—Diego Gutierrez
Assistant Examiner—Yaritza Guadalupe
(74) Attorney, Agent, or Firm—Blakely Sokoloff Taylor & Zafman LLP (57) ABSTRACT

Apparatus for spatial filtering includes a Fourier lens, adapted to collect radiation emitted from a point and to separate the collected radiation into spatial components in a Fourier plane of the lens, and a programmable spatial filter, positioned at the Fourier plane. An image sensor is optically coupled to capture an image of the spatial components of the collected radiation in the Fourier plane, while the components are incident on the filter. A filter controller is coupled to receive and analyze the image captured by the image sensor and, responsive thereto, to control the spatial filter so as to block one or more of the spatial components.

68 Claims, 8 Drawing Sheets

PATTERNED WAFER INSPECTION USING SPATIAL FILTERING

FIELD OF THE INVENTION

The present invention relates generally to optical inspection systems, and specifically to methods and systems for detecting defects on patterned substrates.

BACKGROUND OF THE INVENTION

The use of spatial filtering is well known in systems for optical inspection of patterned substrates, which contain regularly-repeating structures. When the repetitive patterns on such substrates are illuminated with coherent light, they generate constructive interference lobes along well-defined directions. A suitable lens can be used to collect the light reflected from the surface into an image that constitutes a spatial Fourier transform of the substrate pattern. (The lens used for this purpose is referred to as a Fourier transform lens, and the plane in which the Fourier transform image is formed is referred to as the Fourier plane.) The position and extent of the interference lobes in the Fourier plane depend on the period of the pattern and on a scaling factor determined by the wavelength of the incident radiation and the focal length of the lens.

It is known in the art that blocking the interference lobes in the Fourier plane facilitates the detection of defects and pattern irregularities on the substrate. For example, U.S. Pat. No. 3,614,232, to Mathisen, whose disclosure is incorporated herein by reference, describes a spatial filter for detecting defects in photomasks, using a transmission geometry and a simple filter consisting substantially of the negative of the Fourier transform of a defect-free specimen of the microcircuit. U.S. Pat. No. 5,177,559, to Batchelder et al., whose disclosure is likewise incorporated herein by reference, describes a dark field imaging system for inspecting repetitively patterned integrated circuits on a semiconductor wafer. The light scattered from the pattern is filtered with an opaque spatial filter, which attenuates spatial frequency components corresponding to the wafer pattern, and is then converted to an image on an imaging sensor. The substrate is illuminated at a grazing angle to the substrate plane, whereas the scattered light is collected in a direction essentially normal to the surface.

U.S. Pat. No. 4,370,024, to Task et al., whose disclosure is incorporated herein by reference, describes a dynamic binary Fourier filtered imaging system (not specifically for wafer inspection.) The spatial filter used in this case consists of a liquid crystal array, which can be programmed to dynamically produce different opaque filter patterns. Further in this vein, U.S. Pat. No. 5,276,498, to Galbraith et al., whose disclosure is also incorporated herein by reference, describes a system for performing dark field surface inspection of substrates, such as repetitively patterned semiconductor wafers, employing a scanned, focused laser beam and an adaptive spatial filter consisting of a liquid crystal light valve array. The laser beam is incident at a grazing angle on the wafer surface, and the scattered light is also collected at a grazing angle (away from the specularly reflected optical axis), and is measured by a detector. The proper configuration of the spatial filter is determined by illuminating the repetitive pattern with the laser, successively turning each liquid crystal element on and off, and measuring the level of the optical signal at the detector. The pattern is then stored in a computer memory for subsequent use.

U.S. Pat. No. 5,659,390, to Danko, whose disclosure is incorporated herein by reference, describes a system for performing dark field surface inspection of substrates, such as repetitively patterned semiconductor wafers, employing a scanned laser beam and an adaptive spatial filter. Here the spatial filter consists of an optically-addressable liquid crystal spatial light modulator. The laser beam is incident at a grazing angle to the wafer surface, and the scattered light is collected by a detector in a direction normal to the surface. A write beam derived directly from the Fourier-transformed scattered light automatically determines the proper configuration of the spatial filter.

Solutions based on adaptive spatial filters, such as those described in U.S. Pat. Nos. 5,276,498 and 5,659,390, are advantageous in their ability to match the spatial filter to different substrate patterns without the need to replace an optical element. Such filters are capable of generating arbitrary filter patterns, within the constraints of liquid crystal technology. This technology suffers from several shortcomings, however:

1) The transmission range of liquid crystals known in the art is limited to wavelengths in the visible spectrum, roughly 400–700 nm.
2) Liquid crystal modulators have limited contrast ratios, and they are sensitive to polarization and to incidence angle. Therefore, the optical signal transmission of the desired light may be reduced, while the transmission of the undesired light is increased, hence reducing the contrast of the spatial filter itself.
3) When the optically-addressed mechanism is used (as in U.S. Pat. No. 5,659,390), the spatial filter is determined completely automatically. There is no possibility of user intervention to adjust the filter configuration to compensate for unusual substrate features and for different measurement conditions.

SUMMARY OF THE INVENTION

It is an object of some aspects of the present invention to provide improved methods and devices for spatial filtering, and particularly for adaptively blocking undesired spatial frequency components in the Fourier plane.

It is a further object of some aspects of the present invention to provide improved methods and systems for inspection of patterned substrates.

In some preferred embodiments of the present invention, a sample is scanned by a beam of coherent light, and light scattered from the substrate is collected by a Fourier lens. An image sensor acquires an image of the Fourier plane and inputs the image to a filter controller, typically a computer, which analyzes the image to determine an optimal spatial filtering pattern. The computer accordingly controls a programmable spatial filter in the Fourier plane to filter the scattered light using the desired filtering pattern. The use of the image sensor in this manner allows the filtering pattern to be calculated adaptively for the particular substrate and inspection conditions, while simplifying the determination of the filtering pattern, relative to methods known in the art, since the spatial filter itself is not involved in the determination. The filtered light is received by a detector, and the detector signal is analyzed to detect defects in the substrate.

Typically, the sample comprises a patterned substrate, and the optimal filtering pattern is determined, based on the acquired image of the Fourier plane, so as to block spatial frequencies that correspond to the interference lobes generated by the substrate pattern. Additionally or alternatively, the computer maintains a database of optimal filter configurations that have been determined empirically and/or theoretically for different substrate types and measurement conditions. Information from the database is preferably combined with the acquired image to determine the optimal filter pattern to use in each case, either automatically or under the control of an operator. Alternatively, when appropriate, the filter pattern stored in the database may be used, while the acquired image is disregarded. In any case, the filter pattern is preferably determined not only by the acquired image, but also by other considerations, which may be addressed in the database and/or controlled by the user.

In some preferred embodiments of the present invention, the spatial filter comprises an array of micro-optical-electro-mechanical (MOEM) elements. The computer controls the "on" or "off" status of each pixel in the filter by varying the tilt angle of the particular micro-element. In some of these embodiments, the micro-elements comprise mirrors, and the filter operates in a reflective mode. Only the light that is reflected from the "on" pixels reaches the detector, while the light reflected from the "off" pixels is dumped. In other embodiments, the micro-elements comprise shutters, so that the filter operates in a transmissive mode. By comparison with transmissive spatial filters known in the art, however, such as liquid crystal arrays, the present MOEM filters have a much wider spectral range, including ultraviolet (UV) and infrared (IR) wavelengths, and are relatively insensitive to polarization and incidence angle.

Preferably, to reduce diffraction effects in embodiments using reflective spatial filters, the micromirrors are oriented so that in the "off" position they are oriented either parallel to the face of the array, or at a blaze angle chosen so that the diffracted light is concentrated in a lobe away from the detector. Further preferably, the direction of tilt of the micromirrors is perpendicular to the direction of scanning the coherent beam over the substrate, so that the direction of the reflected beam does not change during the scan.

Thus, preferred embodiments of the present invention provide methods of adaptive spatial filtering and substrate inspection that are more flexible and versatile than methods known in the art, in terms of both optical properties of the inspection system and optimization of the spatial filtering patterns that are used. These methods are particularly suited to detection of defects in patterned substrates, such as semiconductor wafers, but they are also useful in other inspection tasks. For example, for detecting particle-type defects, which are elevated above the plane of a substrate, it may be desirable to collect light only at grazing angles, while for defects of the pattern itself, such as missing features, collection at higher elevation angles may be desirable. To deal with these different inspection needs, preferred embodiments of the present invention permit the optical configuration and operating wavelengths of the inspection system to be varied freely, and allow the optimal filter configuration to be determined not only by the repetitive substrate pattern itself, but also by other considerations which may be addressed in the aforementioned database.

There is therefore provided, in accordance with a preferred embodiment of the present invention apparatus for optical inspection of a sample, including:

a radiation source, adapted to irradiate a spot on the sample with coherent radiation;

a Fourier lens, adapted to collect the radiation that is scattered from the spot and to separate the collected radiation into spatial components in a Fourier plane of the lens;

a programmable spatial filter, positioned at the Fourier plane so as to filter the spatial components of the radiation;

a detector, positioned to receive the filtered radiation from the spatial filter, and to generate, responsive to the radiation, a signal for processing to detect a characteristic of the sample;

an image sensor, optically coupled to capture an image of the spatial components of the collected radiation in the Fourier plane, while the components are incident on the filter; and a filter controller, coupled to receive and analyze the image captured by the image sensor and, responsive thereto, to control the spatial filter so as to determine the spatial components to be received by the detector.

Preferably, the spatial filter includes an array of filter elements, which are individually controllable by the filter controller.

In a preferred embodiment, the filter elements include mirrors, which are controllable by the filter controller so as to tilt between a first orientation, in which the mirror reflects the radiation incident thereon toward the detector, and a second orientation, in which the mirror reflects the radiation incident thereon away from the detector. Typically, the array of the mirrors defines an array plane, and in the first orientation, the mirrors are tilted out of the plane, while in the second orientation, the mirrors are oriented substantially parallel to the plane. Alternatively, in the second orientation, the mirrors are oriented relative to the plane at a blaze angle chosen so as to maximize diffraction of the radiation from the mirrors into an order directed away from the detector.

Typically, the array of the mirrors has a periodic structure, and the detector preferably includes a radiation sensor and spatial filtering optics, which are configured to block the radiation diffracted from the array toward the sensor due to the periodic structure of the array, while focusing the radiation reflected from the mirrors in the first orientation onto the sensor.

In another preferred embodiment, the filter elements include shutters, which are controllable by the filter controller so as to move between a first orientation, in which the shutter allows the radiation to pass therethrough toward the detector, and a second orientation, in which the shutter blocks the radiation incident thereon from reaching the detector. Typically, each of the shutters has a respective clear aperture, and the spatial filter further includes an array of microlenses, respectively aligned with the shutters so as to focus the radiation through the clear aperture.

In a further preferred embodiment, the image sensor includes a matrix of sensor elements, and the apparatus includes imaging optics arranged to direct a portion of the radiation collected by the Fourier lens onto the image sensor so that the sensor elements are optically substantially registered with the filter elements, and the controller is adapted to control each of the filter elements responsive to the radiation collected by a respective one of the sensor elements with which the filter element is registered.

Preferably, the apparatus includes a beamsplitter, which is positioned to direct a portion of the radiation collected by the Fourier lens toward the image sensor so that the image sensor can capture the image of the spatial components.

Further preferably, the filter controller is adapted to determine respective intensities of the spatial components in the captured image, and to control the spatial filter responsive to the intensities. Most preferably, the filter controller is adapted to control the spatial filter so as to inhibit the spatial components whose respective intensities exceed a given threshold from reaching the detector.

In a preferred embodiment, the sample includes a substrate having a surface with a pattern formed thereon, so that the spatial components in the Fourier plane include one or more interference lobes formed in the scattered radiation due to the pattern, and wherein the filter controller is adapted to control the spatial filter so as to block at least one of the interference lobes. Typically, responsive to the at least one of the interference lobes being blocked by the spatial filter, the detector is able to detect a defect on the surface of the substrate.

Preferably, the apparatus includes a memory, which is configured to store filter configuration data with respect to different testing parameters, and the filter controller is adapted to receive the testing parameters relevant to the sample under inspection, to read the filter configuration data from the memory corresponding to the relevant testing parameters, and to control the spatial filter responsive to the configuration data. Typically, the sample includes a substrate of a given type, which has known spatial components in the Fourier plane, and the testing parameters include an identification of the substrate type, causing the filter controller to control the spatial filter responsive to the known spatial components, so as to facilitate identification of a defect in the sample.

There is also provided, in accordance with a preferred embodiment of the present invention, apparatus for spatial filtering, including:
  a Fourier lens, adapted to collect radiation emitted from a point and to separate the collected radiation into spatial components in a Fourier plane of the lens;
  a programmable spatial filter, positioned at the Fourier plane;
  an image sensor, optically coupled to capture an image of the spatial components of the collected radiation in the Fourier plane, while the components are incident on the filter; and
  a filter controller, coupled to receive and analyze the image captured by the image sensor and, responsive thereto, to control the spatial filter so as to block one or more of the spatial components.

Preferably, the spatial filter includes an array of filter elements, which are individually controllable by the filter controller, so that each filter element assumes a blocking or a non-blocking status.

There is additionally provided, in accordance with a preferred embodiment of the present invention, optical inspection apparatus, including:
  a radiation source, adapted to irradiate a spot on a sample with coherent radiation and to scan the spot along a line on the sample in a scan direction;
  a Fourier lens, adapted to collect the radiation that is scattered from the spot and to direct the collected radiation to a Fourier plane of the lens;
  a programmable spatial filter positioned at the Fourier plane, the spatial filter including an array of mirrors that are controllable so that each mirror can be individually tilted about an axis parallel to the scan direction between a first orientation and a second orientation; and
  a detector, positioned to receive the collected radiation reflected from the mirrors in the array that are in the first orientation, and not the radiation reflected from the mirrors that are in the second orientation, and to generate, responsive to the radiation, a signal for processing to determine a characteristic of the sample.

Typically, the array of mirrors has a periodic structure, and the detector includes a radiation sensor and spatial filtering optics, which are configured to block the radiation diffracted from the array toward the sensor due to the periodic structure of the array, while focusing the radiation reflected from the mirrors in the first orientation onto the sensor. Preferably, the spatial filtering optics include a second Fourier lens, which is arranged to collect the radiation diffracted from the array and reflected from the mirrors in the first orientation and to direct the collected diffracted and reflected radiation to a second Fourier plane, and an opaque target having a transparent opening, positioned at the second Fourier plane so as to block one or more orders of the diffracted radiation while passing the radiation reflected from the mirrors. Most preferably, the opening includes a slit oriented approximately parallel to the scan direction.

There is further provided, in accordance with a preferred embodiment of the present invention, a spatial filter, including an array of mirrors arranged in a plane, the array being controllable so that each mirror can be individually tilted between a first orientation, in which the mirror is tilted out of the plane so as to deflect radiation that is incident on the mirror toward a detector, and a second orientation, in which the mirror is oriented substantially parallel to the plane so as to deflect the radiation away from the detector.

There is moreover provided, in accordance with a preferred embodiment of the present invention a method for optical inspection of a sample, including:
  irradiating a spot on the sample with coherent radiation;
  collecting a portion of the radiation that is scattered from the spot, and separating the collected radiation into spatial components in a Fourier plane;
  positioning a programmable spatial filter in the Fourier plane so as to filter the spatial components of the radiation;
  receiving the filtered radiation from the spatial filter at a detector, and generating, responsive to the filtered radiation, a signal for processing in order to detect a characteristic of the sample;
  capturing an image of the spatial components of the collected radiation in the Fourier plane, while the components are incident on the filter; and
  analyzing the image captured by the image sensor and, responsive thereto, controlling the spatial filter so as to determine the spatial components to be received by the detector.

There is furthermore provided, in accordance with a preferred embodiment of the present invention, a method for spatial filtering, including:
  collecting radiation emitted from a point, and separating the collected radiation into spatial components in a Fourier plane;
  positioning a programmable spatial filter at the Fourier plane;
  capturing an image of the spatial components of the collected radiation in the Fourier plane, while the components are incident on the filter; and
  analyzing the captured image and, responsive thereto, controlling the spatial filter so as to block one or more of the spatial components.

There is also provided, in accordance with a preferred embodiment of the present invention, a method for optical inspection, including:
  irradiating a spot on a sample with coherent radiation, and scanning the spot along a line on the sample in a scan direction;
  collecting a portion of the radiation that is scattered from the spot, and forming a spatial Fourier transform of the collected radiation in a Fourier plane;

positioning at the Fourier plane a programmable spatial filter including an array of mirrors that are controllable so that each mirror can be individually tilted about an axis parallel to the scan direction between a first orientation and a second orientation; and positioning a detector so as to receive the collected radiation reflected from the mirrors in the array that are in the first orientation, and not the radiation reflected from the mirrors that are in the second orientation, so as to generate, responsive to the radiation, a signal for processing to determine a characteristic of the sample.

There is additionally provided, in accordance with a preferred embodiment of the present invention, a method for spatial filtering, including:

arranging an array of mirrors in a plane; and controlling the mirrors so that each of the mirrors tilts between a first orientation, in which the mirror is tilted out of the plane so as to deflect radiation that is incident on the mirror toward a detector, and a second orientation, in which the mirror is oriented substantially parallel to the plane so as to deflect the radiation away from the detector.

The present invention will be more fully understood from the following detailed description of the preferred embodiments thereof, taken together with the drawings in which:

DETAILED DESCRIPTION OF PREFERRED EMBODIMENTS

Figure 1:
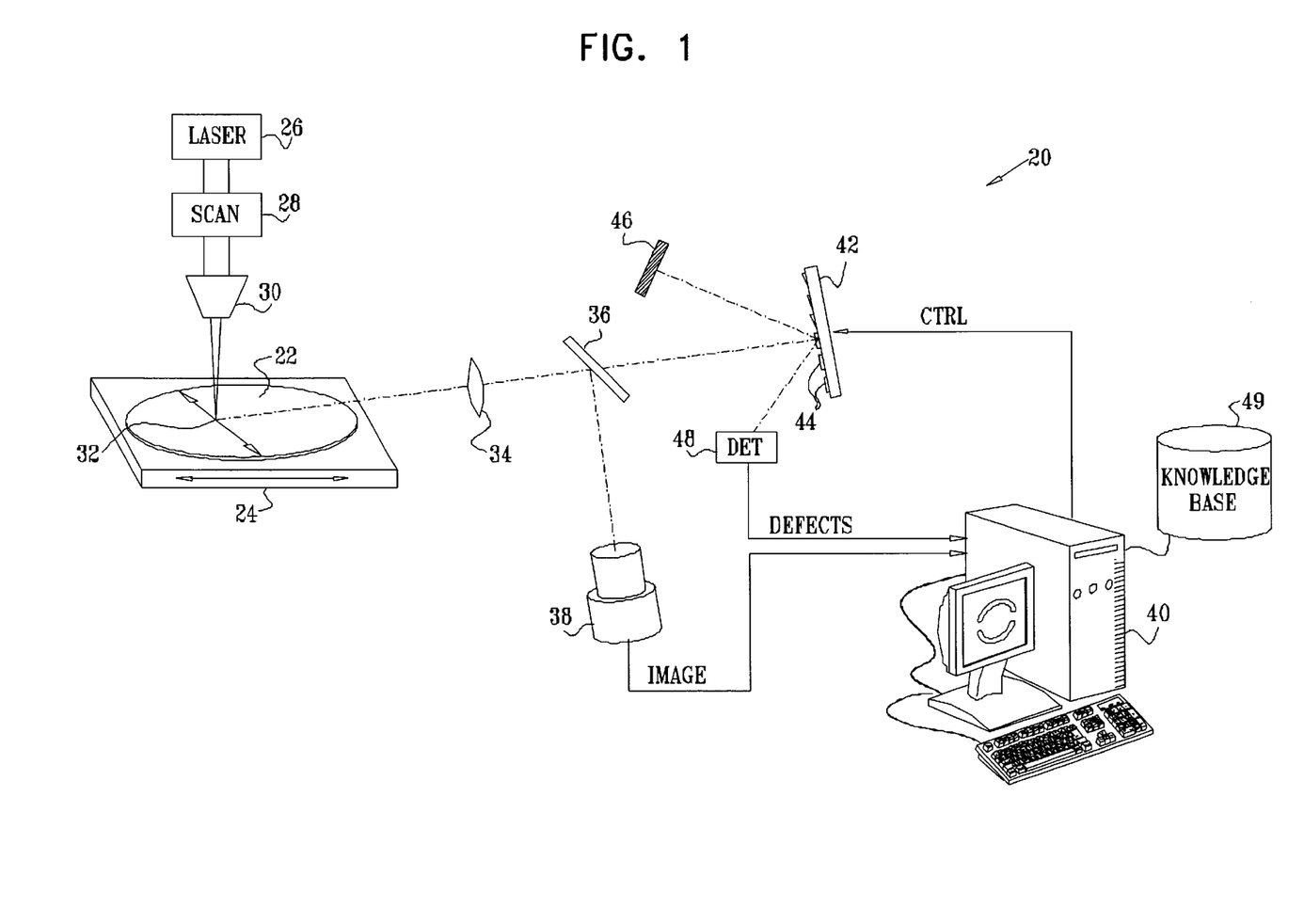
FIG. 1 is a schematic, pictorial illustration of a system for optical inspection, in accordance with a preferred embodiment of the present invention.

FIG. 1 is a schematic, pictorial illustration of a system 20 for automated inspection of a patterned semiconductor wafer 22, in accordance with a preferred embodiment of the present invention. A laser 26 generates a beam of coherent light, which is focused to a spot and scanned over the wafer using a fast scanning mechanism 28, as is known in the art, such as an acousto-optic deflector, rotating polygon mirror, or galvanometric oscillating mirror, together with an objective lens 30. Mechanism 28 scans the beam over the wafer along a scan line 32 in the X-direction (perpendicular to the plane of the page in FIG. 1). A scanning table 24 translates the wafer in the perpendicular Y-direction, so that the laser beam scans the entire wafer in a serpentine fashion. The size of the focused laser spot on wafer 22 is preferably at least 3–4 times that of the pattern repetition period on the wafer, in order to ensure the formation of well-defined interference lobes by the scattered light.

Figure 6:
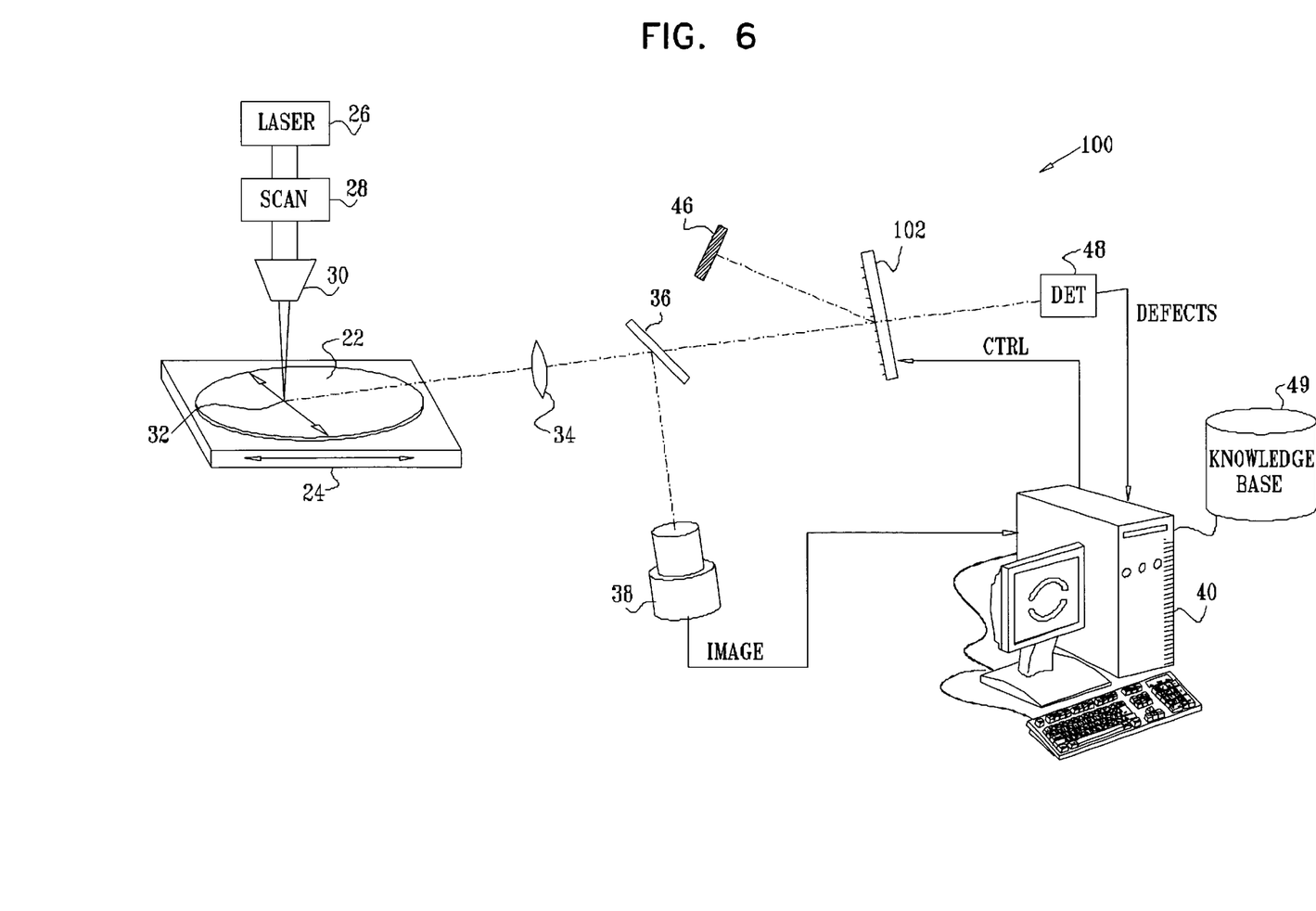
FIG. 6 is a schematic, pictorial illustration of a system for optical inspection, in accordance with another preferred embodiment of the present invention.
Figure 7:
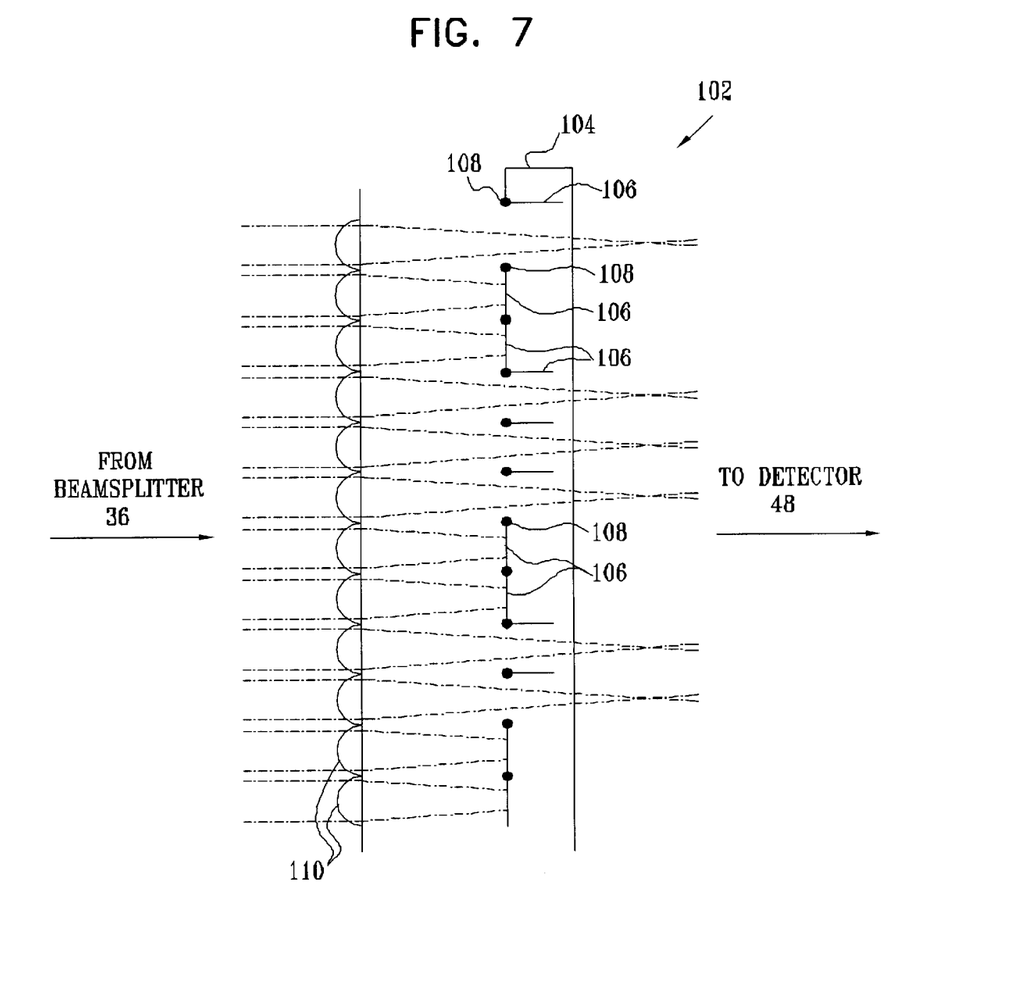
FIG. 7 is a schematic side view of a micro-shutter array configured as a spatial filter, in accordance with a preferred embodiment of the present invention.

The light scattered from wafer 22 into a predetermined dark field solid angle is collected by a Fourier transform lens 34, which forms a spatial Fourier transform of the scattered light distribution at the Fourier transform plane. A micromirror array (MMA) 42 is placed at the Fourier plane to perform spatial filtering of the scattered light. (Alternatively, a microshutter array (MSA) may be used for spatial filtering, as shown in FIGS. 6 and 7 and described with reference thereto.) Array 42 comprises a matrix of mirrors 44, preferably a 256×256 matrix of square mirrors, each 10–20 $\mu$m on a side. The mirrors are preferably coated with dielectric and/or metallic layers so as to provide high reflectivity over the wavelength range of interest, typically from 200 to 800 nm. Suitable micromirror arrays of this type are available, for example, from Texas Instruments, of Dallas, Tex.

The respective angles of orientation of the mirrors are controlled by means of signals applied by a filter controller 40, typically a general-purpose computer with suitable software and input/output interface circuits. Preferably, array 42 is oriented so that mirrors 44 tilt in a direction perpendicular to scan line 32 (i.e., the mirrors rotate about the X-axis). Thus, the relative direction of light reflected from array 42 does not change during the scan. The tilt direction of each mirror 44 determines whether the corresponding pixel in the spatial filter is turned "on" or "off." Light striking the "on" mirrors is reflected toward a detector 48. Light striking the "off" mirrors is reflected toward a light trap 46, which prevents undesirable stray light from reaching detector 48. In response to the light incident on it, detector 48 generates signals, which are analyzed by controller 40 (or by another computer), using methods known in the art, to identify defects on wafer 22.

A small portion of the light collected by Fourier transform lens 34 is split off by an image beamsplitter 36 and is incident on an image sensor 38, such as a charge-coupled device (CCD) camera. Sensor 38, like array 42, is placed at the Fourier plane and thus captures the same Fourier transform image of the reflected light as is incident on the array. The image detected by sensor 38 is input to controller 40, which analyzes the diffraction pattern in order to determine the optimal spatial filtering pattern to be applied by array 42. The controller then instructs the array to set the individual mirrors 44 in the proper configuration. Typically, the mirrors within and immediately surrounding the diffraction lobes generated by the substrate pattern are turned "off," while the remaining pixels are turned "on," to deflect incident light to detector 48.

Optionally, sensor 38 and array 42 are aligned so that the pixels of the image sensor are registered in precise correspondence with mirrors 44 in the array. In this case, each of the mirrors can be controlled based on the intensity of radiation that is incident on the corresponding pixel (or pixels) of the image sensor.

Preferably, in determining the optimal filtering pattern, controller 40 draws on data stored in a knowledge base 49.

Typically, knowledge base 49 contains optimal filter configurations that have been determined empirically and/or theoretically for different substrate types, defect detection tasks and measurement conditions. Information from knowledge base 49 is preferably combined with the image acquired by sensor 38 to determine the optimal filter pattern to use in each case, either automatically or under the control of a user. For example, controller 40 and knowledge base 49 may implement techniques disclosed in U.S. patent application Ser. No. 09/595,902, to Milshtein et al., which is assigned to the assignee of the present patent application and whose disclosure is incorporated herein by reference. This patent application describes a method for a priori determination of the optimal filter configuration by analyzing a high-resolution two-dimensional image of the wafer plane, in combination with the known properties of the materials and three-dimensional configuration of the substrate. Thus, optimal filter configurations for different substrates can be determined in advance and used in combination with the image of the actual, current substrate under inspection. Alternatively, when appropriate, the filter pattern stored in knowledge base 49 may be used, while the acquired image is disregarded.

This latter option is particularly useful for dealing with patterns on wafer 22 that do not exhibit interference lobes, whether because the pattern is not repetitive, or because the lobes created by the pattern do not fall on collection lens 34. For these cases, a general spatial filter configuration may be set based on a priori knowledge of the properties of the inspected substrate and defects. For example, if the primary defect of interest is a particle extending above the surface of the substrate, it is well known that light scattered at lower elevation angles provides the most sensitive defect detection. In this case, micromirror array 42 is preferably controlled so that light scattered from the wafer to higher elevation angles is directed toward beam block 46, while light scattered into lower elevations is directed toward detector 48.

As another example, common features such as conducting lines in the pattern on wafer 22 typically diffract strongly into well-defined azimuthal angles. If the solid angle collected by lens 34 encompasses one of these azimuths, micromirror array 42 is preferably controlled so as to block a region including this azimuth at all elevations.

Other instances of preferential spatial filtering not related to interference lobes generated by the wafer pattern may be known or learned in the course of operating system 20. Information regarding these instances is preferably collected in knowledge base 49, and is then accessed by controller 40 based on operator input indicating the substrate type.

Although the operation of controller 40 is described herein with reference to a particular optical arrangement for spatial filtering, built around micromirror array 42, the principles embodied in controller 40 and in system 20 overall are by no means limited to filtering schemes of this type. These principles may similarly be applied in controlling other sorts of adaptive spatial filters, such as transmissive filters, as are known in the art. It will thus be appreciated that controller 40, together with image sensor 38 and, preferably, knowledge base 49, may be used in operating various types of spatial filters in a wide range of different optical inspection systems and other applications.

Figure 2:
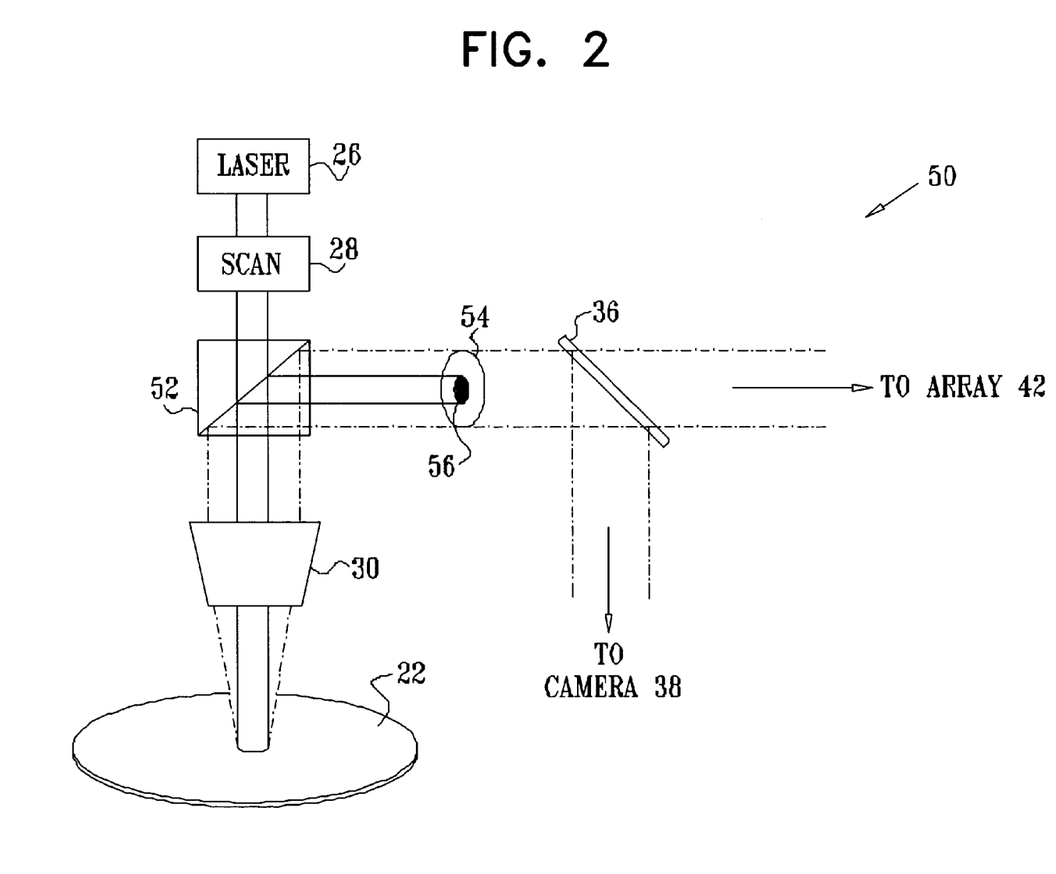
FIG. 2 is a schematic side view of beam delivery and collection optics used in an optical inspection system, in accordance with a preferred embodiment of the present invention.

FIG. 2 is a schematic side view of beam delivery and collection optics 50 for use in system 20, in accordance with another preferred embodiment of the present invention. Optics 50 are similar to those shown in FIG. 1, except that objective lens 30 also serves as the Fourier transform lens. Whereas lens 34 in the configuration of FIG. 1 collects light scattered from wafer 22 at a grazing angle, the configuration shown in FIG. 2 is adapted for collecting high-angle dark field scattering. Notwithstanding these differences in optics 50, the operation of micromirror array 42 and the associated sensor 38 and controller 40 is substantially unchanged relative to that described above.

Objective lens 30 used in the configuration of FIG. 2 must collect scattered and diffracted light over a larger numerical aperture than that of the illumination beam. An objective beamsplitter 52 separates the light reflected from wafer 22 from the incident beam generated by laser 26. Optionally, for enhanced optical efficiency, beamsplitter 52 comprises a polarizing beamsplitter combined with a quarter-wave plate, as is known in the art.

Since the specularly-reflected light from wafer 22 is inherently the zero-order diffraction lobe of the pattern on the wafer surface, this light should always be filtered and not allowed to reach detector 48. Assuming the illumination beam is always of the same size in the Fourier plane, it is preferable to prefilter the zero-order lobe, in order to minimize stray light reaching the detector, as well as preventing saturation of imaging sensor 38. For this purpose, a prefilter 54 with a central blocking region 56 is interposed between objective beamsplitter 52 and image beamsplitter 36.

Whereas in FIGS. 1 and 2, the laser beam is incident on wafer 22 along a normal to the wafer surface, it will be apparent to those skilled in the art that the optical configuration of system 20 can be modified for oblique incidence, as well.

Because the radiation scattered from wafer 22 typically preserves the spatial and temporal coherence of laser 26, the scattered radiation diffracts from the periodic structure of micromirror array 42 much as it would from a two-dimensional diffraction grating. The light incident on the array is diffracted into collimated beams along directions given by the following equation:

$$\sin(\theta) = n\frac{\lambda}{d}.$$

Here $\theta$ is the deflection angle relative to specular reflection from the grating plane, $\lambda$ the wavelength of the light, d the grating pitch (given by the spacing of the micromirrors), and n an index indicating the diffraction order n=0, 1, 2 . . . Assuming the array period (d) is 15 $\mu$m, and $\lambda$=532 nm, the diffraction orders will be separated by about 2°. These diffracted beams contain some finite fraction of the energy incident on array 42. To the extent that any of the diffracted beams impinge on detector 48, they may increase the background level in the detector signal and reduce the sensitivity of system 20 in detecting defects on wafer 22. Such effects should therefore be avoided insofar as possible.

Figure 3A:
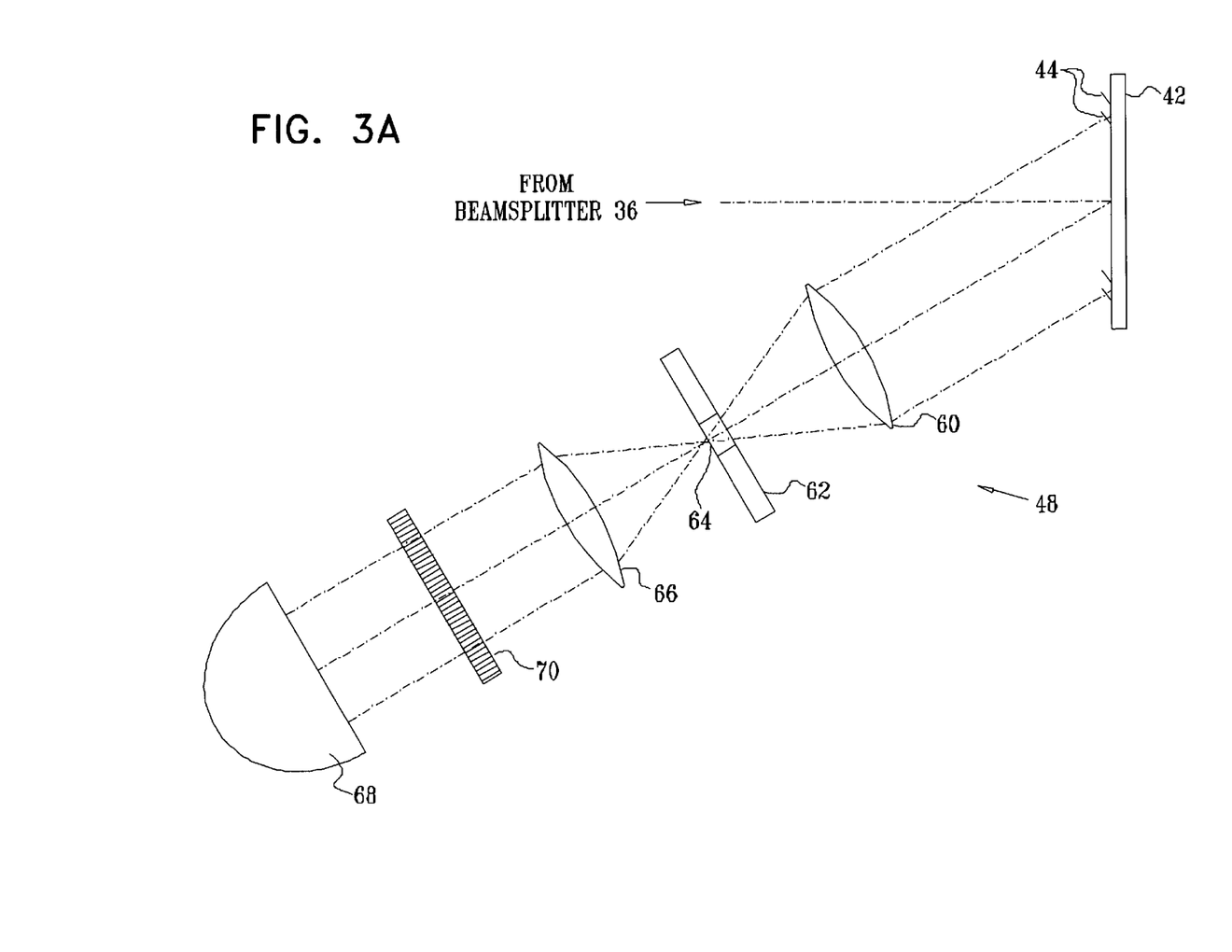
FIG. 3A is a schematic side view of spatial filtering and detection optics used in an optical inspection system, in accordance with a preferred embodiment of the present invention.

FIG. 3A is a schematic side view of detector 48, comprising optics designed to address the problem of diffraction from array 42, in accordance with a preferred embodiment of the present invention. These optics perform an additional spatial filtering step in order to filter out the undesirable diffraction lobes. The light reflected from micromirror array 42 in the "on" direction is focused by a further Fourier lens 60. In the mirror tilt direction (i.e., in the Y-Z plane—the plane of the page in the figures), both the desired defect signal and the undesired diffraction lobes are collimated along well-defined angles. An opaque target 62 with a slit 64 is positioned in the Fourier plane of lens 60, so as to pass the spatial frequency component corresponding to the defect signal, while blocking the diffraction lobes. Slit 64 has a narrow dimension in the tilt direction, to eliminate the diffraction lobes, and a long dimension extending in the X-direction (into the plane of the page), corresponding to the scan direction of the laser beam over wafer 22. The tilt angle of mirrors 44 must be chosen so that the light reflected from array 42 in the "on" direction is sufficiently spaced from the diffraction lobes on either side of it to allow the beams to be separated by slit 64.

The light transmitted through slit 64 is focused by a further objective lens 66 onto a sensor 68, typically a photomultiplier tube (PMT), such as those produced by Hamamatsu Corporation (Hamamatsu, Japan). The output of this sensor is then processed to detect defects on wafer 22. Optionally, a further spatial filter 70 (shown in detail in FIG. 3B) is introduced between lens 66 and sensor 68 to block diffraction lobes distributed in the X-direction that are not blocked by slit 64. The filtering mechanism shown in FIG. 3A is applicable generally in systems that use reflective, pixellated spatial filters. It is typically not necessary in the case of transmissive spatial filters.

Figure 3B:
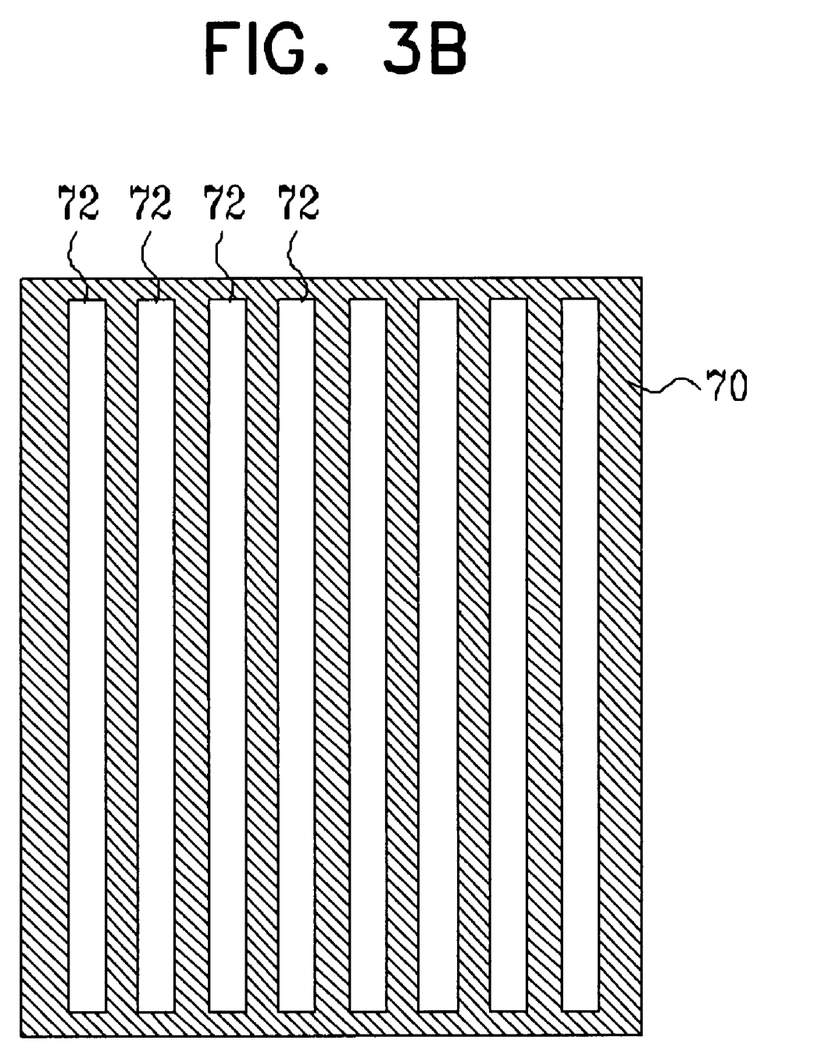
FIG. 3B is a schematic frontal view of a spatial filter used in an optical inspection system, in accordance with a preferred embodiment of the present invention.

FIG. 3B is a schematic frontal view of filter 70, in accordance with a preferred embodiment of the present invention. While target 62 with slit 64 is effective in blocking stray light due to diffraction in the Y-Z plane, there may be additional diffraction lobes distributed in the X-direction that are not blocked by this element. These additional lobes are typically generated by diffraction from the vertical edges of mirrors 44 in array 42 and the regions between the vertical edges. Filter 70 is preferably introduced following lens 66 in order to remove these lobes. As shown in the figure, filter 70 comprises an array of slits 72, which are positioned to pass the optical signal reflected from mirrors 44 while blocking the light scattered from the vertical edges of the mirrors and the regions in between.

Figure 4A:
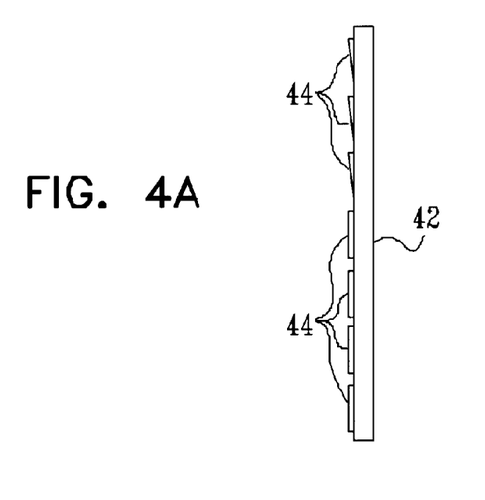
FIG. 4A is a schematic side view of a micromirror array configured as a spatial filter, in accordance with a preferred embodiment of the present invention.

FIG. 4A is a schematic side view of micromirror array 42, showing preferred "on" and "off" mirror tilt angles, in accordance with a preferred embodiment of the present invention. In this example, the three upper mirrors 44 are shown in the "on" position, while the lower mirrors are in the "off" position. Preferably, the "off" tilt angle is set to zero, i.e., the mirrors are parallel to the plane of the grating, as shown in this figure. As a result, the effective modulation depth of the grating formed by the micromirrors is minimized, and the amplitude of the undesirable diffraction lobes is consequently minimized.

Figure 4B:
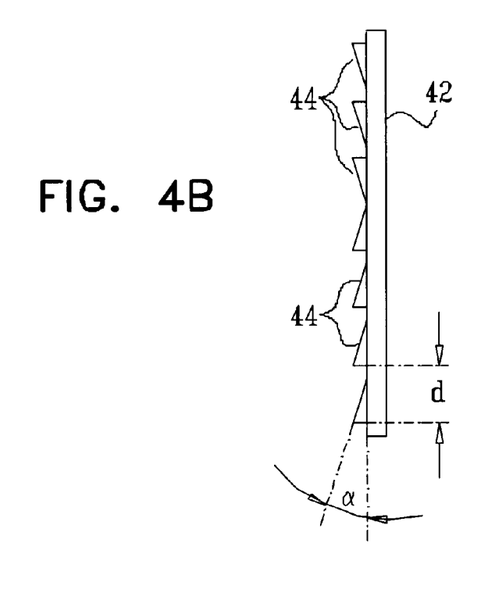
FIG. 4B is a schematic side view of a micromirror array configured as a spatial filter, in accordance with another preferred embodiment of the present invention.

FIG. 4B is a is a schematic side view of micromirror array 42, showing preferred "on" and "off" mirror tilt angles, in accordance with another preferred embodiment of the present invention. In this case, the "off" tilt angle is set to a value $\alpha$, chosen to meet the blaze condition for optimal diffraction into the diffraction order that is directed toward beam block 46. For a given mirror pitch d, the blaze condition requires that $\alpha$ satisfy the equation: $\sin\alpha = \lambda \cdot n \cdot d/2$, wherein $\lambda$ is the wavelength, and n is an integer.

Figure 5:
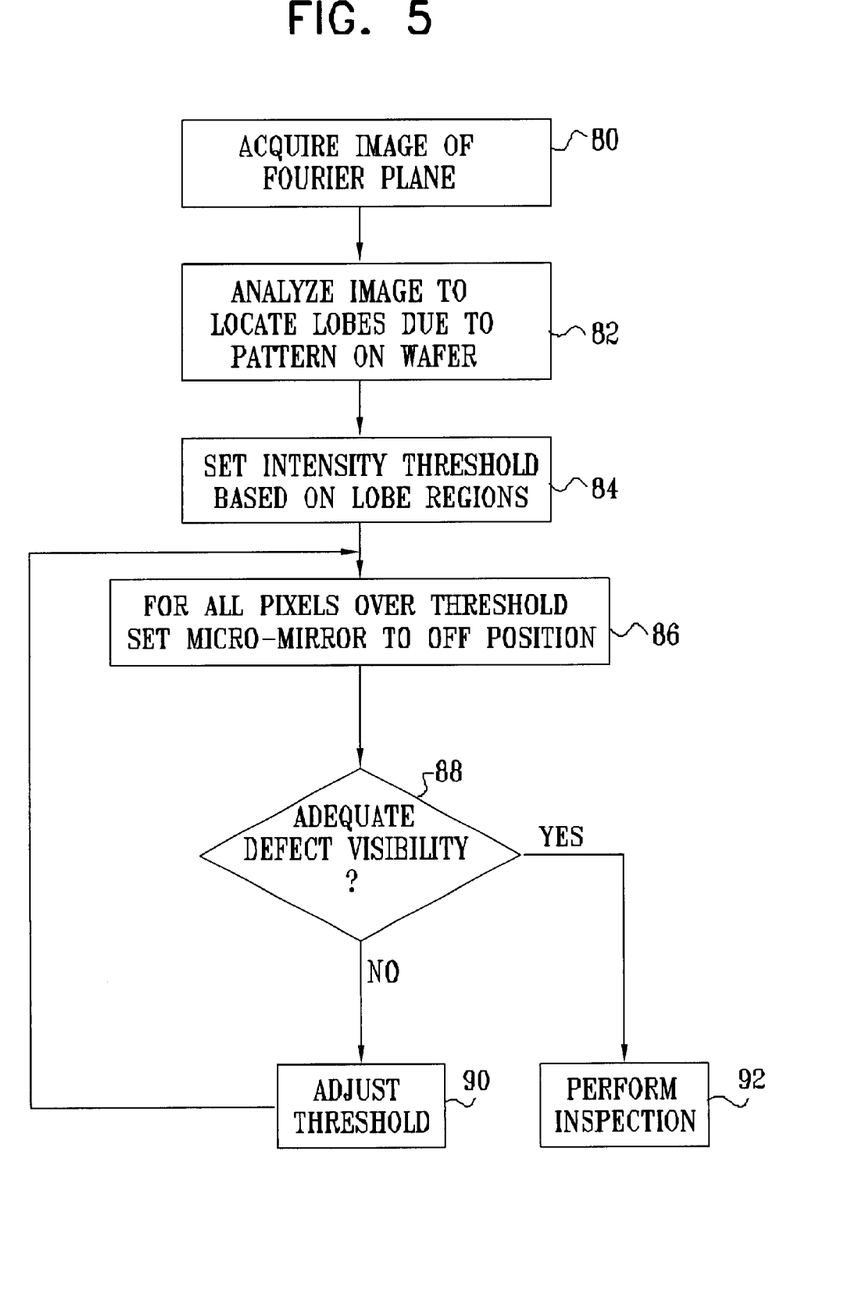
FIG. 5 is a flow chart that schematically illustrates a method for adjusting a spatial filter, in accordance with a preferred embodiment of the present invention.

FIG. 5 is a flow chart that schematically illustrates a method for controlling micromirror array 42, in accordance with a preferred embodiment of the present invention. This method is applicable to inspected patterns exhibiting interference lobes or other instances of well-defined bright regions in the Fourier plane of lens 34. Image sensor 38 acquires an image of the Fourier plane, at an image acquisition step 80. Controller 40 analyzes the acquired image to determine the exact position and extent of the lobes or other bright regions, at an image analysis step 82. Based on this analysis, the controller decides which micromirrors to turn "on" and which to turn "off," in order to prevent the light in the interference lobes from reaching detector 48. As noted above, controller 40 may set the configuration of array 42 autonomously, based only on the image acquired by sensor 38, or it may receive additional inputs from knowledge base 49 and/or from the operator of system 20.

In the embodiment shown in FIG. 5, controller 40 sets an intensity threshold based on the bright and dark regions in the image acquired by sensor 38, at a threshold setting step 84. The threshold value may also be set interactively by the operator, or the value corresponding to the type and other details of wafer 22 may be read from knowledge base 49. For each pixel in the image that has an intensity above the threshold, the corresponding mirror 44 in array 42 is set to the "off" position, at a filter configuration step 86. Preferably, while the threshold is being determined, system 20 is set to continuously illuminate a region of wafer 22 that is known to contain the repetitive pattern.

After setting the positions of the micromirrors, the signal output by detector 48 is evaluated to determine whether the threshold level is such as to provide optimal defect detection, at an evaluation step 88. If not, the threshold value is preferably adjusted up or down, at a threshold adjustment step 90, and steps 86 and 88 are repeated. Once the optimal threshold value has been found, inspection of wafer 22 for defects can proceed, at an inspection step 92. The threshold value thus determined is preferably stored in knowledge base 49 for subsequent use on other, similar wafers. This value may be further refined upon successive inspections during which the effectiveness of each threshold value in detecting the defects is determined.

FIG. 6 is a schematic, pictorial illustration of a system 100 for automated inspection of wafer 22, in accordance with another preferred embodiment of the present invention. System 100 is substantially similar to system 20, as shown and described above, except that in place of micromirror array 42, system 100 uses a transmissive microshutter array (MSA) 102 to spatially filter the light scattered from wafer 22. Detector 48 is therefore placed behind array 102, to receive light filtered through the array. This configuration is less sensitive to diffracted stray light than the reflective arrangement shown in FIG. 1, and can be made to operate over a wide range of wavelengths. Various microshutter technologies are known in the art, and may be applied to produce array 102. Exemplary microshutter arrays are described in U.S. Pat. Nos. 5,784,189, 5,808,384, 6,248,509, 6,288,824 and 6,313,937, whose disclosures are incorporated herein be reference.

FIG. 7 is a schematic side view of array 102, in accordance with a preferred embodiment of the present invention. Array 102 comprises a micro-optical electro-mechanical (MOEM) assembly 104, in which a matrix of shutters 106 are mounted to open and close on respective axes 108. Each shutter is actuated by its own micro-mechanism (not shown in the figure), which may block a portion of the shutter aperture. Therefore, a matrix of microlenses 110 is preferably positioned in front of assembly 104, in order to focus the incident light through the clear apertures of the shutters.

As the laser beam scans wafer 22 along scan line 32 in the X-direction (into the page in the view of FIG. 7), the focal point of each microlens 110 will scan across the corresponding shutter aperture in the X-direction, as well. Assuming that the entire scan covers an angular range of $2\alpha$, and the shutter apertures have dimensions $d_x$ and $d_y$ in the X- and Y-directions, respectively, microlenses 110 should have focal length f and numerical aperture NA that satisfy the following criteria:

$$d_y > \frac{\lambda}{NA},$$

and $$d_x > \frac{\lambda}{NA} + 2f \cdot \sin\alpha.$$

When these criteria are met, the effective transmittance of the optical signal through the open pixels of array 102 is maximized.

As noted above, although preferred embodiments are described herein with particular reference to inspection of patterned semiconductor wafers, the principles of the present invention may also be applied in other areas of spatial filtering and optical inspection, especially inspection of reticles, printed circuits and flat panel displays. It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus for optical inspection of a sample, comprising:
   a radiation source, adapted to irradiate a spot on the sample with coherent radiation;
   a Fourier lens, adapted to collect the radiation that is scattered from the spot and to separate the collected radiation into spatial components in a Fourier plane of the lens;
   a programmable spatial filter, positioned at the Fourier plane so as to filter the spatial components of the radiation;
   a detector, positioned to receive the filtered radiation from the spatial filter, and to generate, responsive to the radiation, a signal for processing to detect a characteristic of the sample;
   an image sensor, optically coupled to capture an image of the spatial components of the collected radiation in the Fourier plane, while the components are incident on the filter; and
   a filter controller, coupled to receive and analyze the image captured by the image sensor and, responsive thereto, to control the spatial filter so as to determine the spatial components to be received by the detector.

2. Apparatus according to claim 1, wherein the spatial filter comprises an array of filter elements, which are individually controllable by the filter controller.

3. Apparatus according to claim 2, wherein the filter elements comprise mirrors, which are controllable by the filter controller so as to tilt between a first orientation, in which the mirror reflects the radiation incident thereon toward the detector, and a second orientation, in which the mirror reflects the radiation incident thereon away from the detector.

4. Apparatus according to claim 3, wherein the array of the mirrors defines an array plane, and wherein in the first orientation, the mirrors are tilted out of the plane, while in the second orientation, the mirrors are oriented substantially parallel to the plane.

5. Apparatus according to claim 3, wherein the array of the mirrors defines an array plane, and wherein in the second orientation, the mirrors are oriented relative to the plane at a blaze angle chosen so as to maximize diffraction of the radiation from the mirrors into an order directed away from the detector.

6. Apparatus according to claim 3, wherein the radiation source comprises scanning optics, which are adapted to scan the spot along a line on the sample in a scan direction, and wherein the mirrors are adapted to tilt between the first and second orientations about a tilt axis that is parallel to the scan direction.

7. Apparatus according to claim 3, wherein the array of the mirrors has a periodic structure, and wherein the detector comprises a radiation sensor and spatial filtering optics, which are configured to block the radiation diffracted from the array toward the sensor due to the periodic structure of the array, while focusing the radiation reflected from the mirrors in the first orientation onto the sensor.

8. Apparatus according to claim 2, wherein the filter elements comprise shutters, which are controllable by the filter controller so as to move between a first orientation, in which the shutter allows the radiation to pass therethrough toward the detector, and a second orientation, in which the shutter blocks the radiation incident thereon from reaching the detector.

9. Apparatus according to claim 8, wherein each of the shutters has a respective clear aperture, and wherein the spatial filter further comprises an array of microlenses, respectively aligned with the shutters so as to focus the radiation through the clear aperture.

10. Apparatus according to claim 2, wherein the image sensor comprises a matrix of sensor elements, and comprising imaging optics arranged to direct a portion of the radiation collected by the Fourier lens onto the image sensor so that the sensor elements are optically substantially registered with the filter elements, and wherein the controller is adapted to control each of the filter elements responsive to the radiation collected by a respective one of the sensor elements with which the filter element is registered.

11. Apparatus according to claim 1, and comprising a beamsplitter, which is positioned to direct a portion of the radiation collected by the Fourier lens toward the image sensor so that the image sensor can capture the image of the spatial components.

12. Apparatus according to claim 1, wherein the filter controller is adapted to determine respective intensities of the spatial components in the captured image, and to control the spatial filter responsive to the intensities.

13. Apparatus according to claim 12, wherein the filter controller is adapted to control the spatial filter so as to inhibit the spatial components whose respective intensities exceed a given threshold from reaching the detector.

14. Apparatus according to claim 1, wherein the sample comprises a substrate having a surface with a pattern formed thereon, so that the spatial components in the Fourier plane include one or more interference lobes formed in the scattered radiation due to the pattern, and wherein the filter controller is adapted to control the spatial filter so as to block at least one of the interference lobes.

15. Apparatus according to claim 14, wherein responsive to the at least one of the interference lobes being blocked by the spatial filter, the detector is able to detect a defect on the surface of the substrate.

16. Apparatus according to claim 1, and comprising a memory, which is configured to store filter configuration data with respect to different testing parameters, and wherein the filter controller is adapted to receive the testing parameters relevant to the sample under inspection, to read the filter configuration data from the memory corresponding to the relevant testing parameters, and to control the spatial filter responsive to the configuration data.

17. Apparatus according to claim 16, wherein the sample comprises a substrate of a given type, which has known spatial components in the Fourier plane, and wherein the testing parameters include an identification of the substrate type, causing the filter controller to control the spatial filter responsive to the known spatial components.

18. Apparatus according to claim 16, wherein the testing parameters include an indication that the sample is to be inspected for a defect of a given type, and wherein the indication causes the filter controller to control the spatial filter so as to facilitate identification of the defect.

19. Apparatus according to claim 1, wherein the signal generated by the detector is indicative of a defect in the sample.

20. Apparatus for spatial filtering, comprising:
a Fourier lens, adapted to collect radiation emitted from a point and to separate the collected radiation into spatial components in a Fourier plane of the lens;
a programmable spatial filter, positioned at the Fourier plane;
an image sensor, optically coupled to capture an image of the spatial components of the collected radiation in the Fourier plane, while the components are incident on the filter; and
a filter controller, coupled to receive and analyze the image captured by the image sensor and, responsive thereto, to control the spatial filter so as to block one or more of the spatial components.

21. Apparatus according to claim 20, wherein the spatial filter comprises an array of filter elements, which are individually controllable by the filter controller, so that each filter element assumes a blocking or a non-blocking status.

22. Apparatus according to claim 21, wherein the filter elements comprise mirrors, which are controllable by the filter controller so as to tilt between a first orientation, in which the mirror assumes the non-blocking status, so as to reflect the radiation incident thereon toward a detector, and a second orientation, in which the mirror assumes the blocking status, so as to reflect the radiation incident thereon away from the detector.

23. Apparatus according to claim 22, wherein the array of the mirrors defines an array plane, and wherein in the first orientation, the mirrors are tilted out of the plane, while in the second orientation, the mirrors are oriented substantially parallel to the plane.

24. Apparatus according to claim 22, wherein the array of the mirrors defines an array plane, and wherein in the second orientation, the mirrors are oriented relative to the plane at a blaze angle chosen so as to maximize diffraction of the radiation from the mirrors into an order directed away from the detector.

25. Apparatus according to claim 21, wherein the filter elements comprise shutters, which are controllable by the filter controller so as to move between a first orientation, in which the shutter assumes the non-blocking status, so as to allow the radiation to pass therethrough toward a detector, and a second orientation, in which the shutter assumes the blocking status, so as to block the radiation incident thereon from reaching the detector.

26. Apparatus according to claim 25, wherein each of the shutters has a respective clear aperture, and wherein the spatial filter further comprises an array of microlenses, respectively aligned with the shutters so as to focus the radiation through the clear aperture.

27. Apparatus according to claim 21, wherein the image sensor comprises a matrix of sensor elements, and comprising imaging optics arranged to direct a portion of the radiation collected by the Fourier lens onto the image sensor so that the sensor elements are optically substantially registered with the filter elements.

28. Apparatus according to claim 27, wherein the controller is adapted to control each of the filter elements responsive to the radiation collected by a respective one of the sensor elements with which the filter element is registered.

29. Apparatus according to claim 20, and comprising a beamsplitter, which is positioned to direct a portion of the radiation collected by the Fourier lens toward the image sensor so that the image sensor can capture the image of the spatial components.

30. Apparatus according to claim 20, wherein the filter controller is adapted to control the spatial filter so as to block the spatial components that have respective intensities above a given threshold.

31. Optical inspection apparatus, comprising:
a radiation source, adapted to irradiate a spot on a sample with coherent radiation and to scan the spot along a line on the sample in a scan direction;
a Fourier lens, adapted to collect the radiation that is scattered from the spot and to direct the collected radiation to a Fourier plane of the lens;
a programmable spatial filter positioned at the Fourier plane, the spatial filter comprising an array of mirrors that are controllable so that each mirror can be individually tilted; about an axis parallel to the scan direction between a first orientation and a second orientation;
a detector, positioned to receive the collected radiation reflected from the mirrors in the array that are in the first orientation, and not the radiation reflected from the mirrors that are in the second orientation, and to generate, responsive to the radiation, a signal for processing to determine a characteristic of the sample;
an image sensor, optically coupled to capture an image of spatial components of the collected radiation in the Fourier plane, while the components are incident on the filter; and
a filter controller, coupled to receive and analyze the image captured by the image sensor and, responsive thereto, to control the spatial filter so as to block one or more of the spatial components.

32. Apparatus according to claim 31, wherein the array of mirrors has a periodic structure, and wherein the detector comprises a radiation sensor and spatial filtering optics, which are configured to block the radiation diffracted from the array toward the sensor due to the periodic structure of the array, while focusing the radiation reflected from the mirrors in the first orientation onto the sensor.

33. Apparatus according to claim 32, wherein the Fourier lens that is adapted to collect the radiation scattered from the spot comprises a first Fourier lens, and the Fourier plane of the lens comprises a first Fourier plane, and wherein the spatial filtering optics comprise:
a second Fourier lens, which is arranged to collect the radiation diffracted from the array and reflected from the mirrors in the first orientation and to direct the collected diffracted and reflected radiation to a second Fourier plane; and an opaque target having a transparent opening, positioned at the second Fourier plane so as to block one or more orders of the diffracted radiation while passing the radiation reflected from the mirrors.

34. Apparatus according to claim 33, wherein the opening comprises a slit oriented approximately parallel to the scan direction.

35. Apparatus according to claim 31, wherein the array of mirrors defines an array plane, and wherein in the first orientation, the mirrors are tilted out of the plane, while in the second orientation, the mirrors are oriented substantially parallel to the plane.

36. Apparatus according to claim 31, wherein the array of the mirrors defines an array plane, and wherein in the second orientation, the mirrors are oriented relative to the plane at a blaze angle chosen so as to maximize diffraction of the radiation from the mirrors into an order directed away from the detector.

37. A method for optical inspection of a sample, comprising:

irradiating a spot on the sample with coherent radiation;

collecting a portion of the radiation that is scattered from the spot, and separating the collected radiation into spatial components in a Fourier plane;

positioning a programmable spatial filter in the Fourier plane so as to filter the spatial components of the radiation;

receiving the filtered radiation from the spatial filter at a detector, and generating, responsive to the filtered radiation, a signal for processing in order to detect a characteristic of the sample;

capturing on an image sensor an image of the spatial components of the collected radiation in the Fourier plane, while the components are incident on the filter; and analyzing the image captured by the image sensor and, responsive thereto, controlling the spatial filter so as to determine the spatial components to be received by the detector.

38. A method according to claim 37, wherein positioning the spatial filter comprises positioning an array of individually-controllable filter elements.

39. A method according to claim 38, wherein the filter elements comprise mirrors, and wherein controlling the spatial filter comprises causing the mirrors to tilt between a first orientation, in which the mirrors reflect the radiation incident thereon toward the detector, and a second orientation, in which the mirrors reflect the radiation incident thereon away from the detector.

40. A method according to claim 39, wherein the array of the mirrors defines an array plane, and wherein in the first orientation, the mirrors are tilted out of the plane, while in the second orientation, the mirrors are oriented substantially parallel to the plane.

41. A method according to claim 39, wherein the array of the mirrors defines an array plane, and wherein in the second orientation, the mirrors are oriented relative to the plane at a blaze angle chosen so as to maximize diffraction of the radiation from the mirrors into an order directed away from the detector.

42. A method according to claim 39, and comprising scanning the spot along a line on the sample in a scan direction, and wherein causing the mirrors to tilt comprises tilting the mirrors between the first and second orientations about a tilt axis that is parallel to the scan direction.

43. A method according to claim 39, wherein the array of the mirrors has a periodic structure, and wherein the detector comprises a radiation sensor, and comprising filtering the radiation so as to block the radiation diffracted from the array toward the sensor due to the periodic structure of the array, while focusing the radiation reflected from the mirrors in the first orientation onto the sensor.

44. A method according to 38, claim wherein the filter elements comprise shutters, and wherein controlling the spatial filter comprises causing the shutters to move between a first orientation, in which the shutter allows the radiation to pass therethrough toward the detector, and a second orientation, in which the shutter blocks the radiation incident thereon from reaching the detector.

45. A method according to claim 44, wherein each of the shutters has a respective clear aperture, and comprising aligning an array of microlenses with the shutters so as to focus the radiation through the clear aperture.

46. A method according to claim 38, wherein capturing the image comprises imaging the Fourier plane using a sensor comprising a matrix of sensor elements, which are optically substantially registered with the filter elements, and wherein controlling the spatial filter comprises controlling each of the filter elements responsive to the radiation collected by a respective one of the sensor elements with which the filter element is registered.

47. A method according to claim 37, wherein analyzing the image comprises determining respective intensities of the spatial components in the captured image, and wherein controlling the spatial filter comprises controlling the filter responsive to the intensities.

48. A method according to claim 47, wherein controlling the filter comprises inhibiting the spatial components whose respective intensities exceed a given threshold from reaching the detector.

49. A method according to claim 37, wherein the sample comprises a substrate having a surface with a pattern formed thereon, so that the spatial components in the Fourier plane include one or more interference lobes formed in the scattered radiation due to the pattern, and wherein controlling the spatial filter comprises causing the filter to block at least one of the interference lobes.

50. A method according to claim 49, wherein causing the filter to block the at least one of the interference lobes comprises reducing a background level in the signal generated by the detector so as to enable a defect on the surface of the substrate to be detected.

51. A method according to claim 37, and comprising storing filter configuration data with respect to different testing parameters, and wherein controlling the spatial filter comprises receiving the testing parameters relevant to the sample under inspection and reading the filter configuration data from the memory corresponding to the relevant testing parameters, and controlling the spatial filter responsive to the configuration data read from the memory.

52. A method according to claim 51, wherein the sample comprises a substrate of a given type, which has known spatial components in the Fourier plane, and wherein receiving the testing parameters comprises receiving an identification of the substrate type, and wherein controlling the spatial the filter comprises controlling the spatial filter responsive to the known spatial components.

53. A method according to claim 51, wherein receiving the testing parameters comprises receiving an indication that the sample is to be inspected for a defect of a given type, and wherein controlling the spatial filter comprises controlling the spatial filter responsive to the indication so as to facilitate identification of the defect.

54. Apparatus according to claim 37, wherein generating the signal comprises producing the signal so as to indicate a defect in the sample.

55. A method for spatial filtering, comprising:

collecting radiation emitted from a point, and separating the collected radiation into spatial components in a Fourier plane;

positioning a programmable spatial filter at the Fourier plane;

capturing an image of the spatial components of the collected radiation in the Fourier plane, while the components are incident on the filter; and analyzing the captured image and, responsive thereto, controlling the spatial filter so as to block one or more of the spatial components.

56. A method according to claim 55, wherein positioning the spatial filter comprises positioning an array of filter elements, and wherein controlling the spatial filter comprises controlling the filter elements so that each filter element assumes a blocking or a non-blocking status.

57. A method according to claim 56, wherein the filter elements comprise mirrors, and wherein controlling the filter elements comprises tilting the mirrors between a first orientation, in which the mirrors assume the non-blocking status, so as to reflect the radiation incident thereon toward a detector, and a second orientation, in which the mirrors assume the blocking status, so as to reflect the radiation incident thereon away from the detector.

58. A method according to claim 57, wherein the array of the mirrors defines an array plane, and wherein in the first orientation, the mirrors are tilted out of the plane, while in the second orientation, the mirrors are oriented substantially parallel to the plane.

59. A method according to claim 57, wherein the array of the mirrors defines an array plane, and wherein in the second orientation, the mirrors are oriented relative to the plane at a blaze angle chosen so as to maximize diffraction of the radiation from the mirrors into an order directed away from the detector.

60. A method according to claim 56, wherein the filter elements comprise shutters, and wherein controlling the filter elements comprises moving the shutters between a first orientation, in which the shutter assumes the non-blocking status, so as to allow the radiation to pass therethrough toward a detector, and a second orientation, in which the shutter assumes the blocking status, so as to block the radiation incident thereon from reaching the detector.

61. A method according to claim 60, wherein each of the shutters has a respective clear aperture, and comprising aligning an array of microlenses with the shutters so as to focus the radiation through the clear aperture.

62. A method according to claim 56, wherein capturing the image comprises capturing the image on a matrix of sensor elements, which are optically substantially registered with the filter elements.

63. A method according to claim 62, wherein controlling the spatial filter comprises controlling each of the filter elements responsive to the radiation collected by a respective one of the sensor elements with which the filter element is registered.

64. A method according to claim 55, wherein controlling the spatial filter comprises blocking the spatial components that have respective intensities above a given threshold.

65. A method for optical inspection, comprising:

irradiating a spot on a sample with coherent radiation, and scanning the spot along a line on the sample in a scan direction;

collecting a portion of the radiation that is scattered from the spot, and forming a spatial Fourier transform of the collected radiation in a Fourier plane;

positioning at the Fourier plane a programmable spatial filter comprising an array of mirrors that are controllable so that each mirror can be individually tilted about an axis parallel to the scan direction between a first orientation and a second orientation; and positioning a detector so as to receive the collected radiation reflected from the mirrors in the array that are in the first orientation, and not the radiation reflected from the mirrors that are in the second orientation, so as to generate, responsive to the radiation, a signal for processing to determine a characteristic of the sample;

positioning an image sensor so that it is optically coupled to capture an image of spatial components of the collected radiation in the Fourier plane while the components are incident on the filter; and analyzing the image captured by the image sensor with a filter controller coupled to receive and, in response thereto, control the spatial filter so as to block one or more of the spatial components.

66. A method according to claim 65, wherein the array of mirrors has a periodic structure, and wherein the detector comprises a radiation sensor, and comprising filtering the radiation so as to block the radiation diffracted from the array toward the sensor due to the periodic structure of the array, while focusing the radiation reflected from the mirrors in the first orientation onto the sensor.

67. A method according to claim 65, wherein the array of mirrors defines an array plane, and wherein in the first orientation, the mirrors are tilted out of the plane, while in the second orientation, the mirrors are oriented substantially parallel to the plane.

68. A method according to claim 65, wherein the array of the mirrors defines any array plane, and wherein in the second orientation, the mirrors are oriented relative to the plane at a blaze angle chosen so as to maximize diffraction of the radiation from the mirrors into an order directed away from the detector.

* * * * *